United States Patent

Stockstill

(10) Patent No.: US 6,682,344 B1
(45) Date of Patent: Jan. 27, 2004

(54) ORTHODONTIC BRACKET PLACEMENT DEVICE AND COORDINATED BRACKET PLACEMENT SYSTEM

(75) Inventor: John W. Stockstill, Evans, GA (US)

(73) Assignee: MCG Research Institute, Augusta, GA (US)

( * ) Notice: Subject to any disclaimer, the term of this patent is extended or adjusted under 35 U.S.C. 154(b) by 0 days.

(21) Appl. No.: 10/106,764

(22) Filed: Mar. 27, 2002

(51) Int. Cl.[7] .......................... A61C 3/00; A61C 19/04
(52) U.S. Cl. ..................... 433/3; 433/31; 433/72
(58) Field of Search .................... 433/3, 24, 72, 433/75, 141, 143, 31; 206/368, 369, 370, 63.5

(56) References Cited

U.S. PATENT DOCUMENTS

| | | | |
|---|---|---|---|
| 3,871,098 A | | 3/1975 | Dean |
| 4,422,849 A | | 12/1983 | Diamond |
| 4,474,555 A | | 10/1984 | Diamond |
| 4,478,576 A | | 10/1984 | Maijer et al. |
| 4,850,864 A | * | 7/1989 | Diamond .................. 433/3 |
| 5,312,248 A | | 5/1994 | Zandkarimi |
| 5,487,660 A | * | 1/1996 | Good ....................... 433/3 |
| 5,542,842 A | | 8/1996 | Andreiko et al. |
| 5,741,267 A | * | 4/1998 | Jorneus et al. ........... 433/72 |
| 5,810,582 A | * | 9/1998 | Doyle ...................... 206/369 |
| 6,213,767 B1 | * | 4/2001 | Dixon et al. ............. 206/369 |
| 6,290,495 B1 | | 9/2001 | Jabri |
| 6,296,482 B1 | | 10/2001 | Kapit |
| 6,447,291 B2 | * | 9/2002 | Kim ........................ 433/3 |

* cited by examiner

Primary Examiner—Todd E. Manahan
(74) Attorney, Agent, or Firm—Jagtiani +Guttag (57) ABSTRACT

The present invention provides an orthodontic bracket placement device comprising a horizontal bracket engaging element for engaging an orthodontic bracket; and a vertical shaft extending from the horizontal bracket engaging element, the shaft including a plurality of indicia for aligning with the incisal edge of a tooth when the bracket placement device is used to place an orthodontic bracket engaged by the engaging element on the tooth. A method is also provided for placing an orthodontic bracket on a tooth comprising placing the orthodontic bracket on the tooth at a particular vertical position on the tooth using a bracket placement device by engaging a horizontal bracket engaging element of the device with a bracket and aligning one of a plurality of indicia on the bracket placement device with the incisal edge of the tooth; and adhering the orthodontic bracket to the tooth. Kits comprising bracket placement devices of the present invention are also provided.

58 Claims, 9 Drawing Sheets

ORTHODONTIC BRACKET PLACEMENT DEVICE AND COORDINATED BRACKET PLACEMENT SYSTEM

BACKGROUND OF THE INVENTION

1. Field of the Invention

The present invention relates generally to dental and orthodontic equipment, and more particularly to an orthodontic bracket placement device and coordinated bracket placement method.

2. Description of the Prior Art

Orthodontic brackets are dental devices used to guide tooth movement during orthodontic treatment. These brackets are typically made of either stainless steel, gold or ceramic material. Brackets are manufactured with specific "prescriptions" which take into account the ideal mesiodistal tip of teeth, labiolingual torque of teeth, and the facial-lingual projection of the teeth (in-out). This prescription makes it imperative that specific brackets be used for specific teeth since the dimensions listed above are different to take into account the anatomical and functional differences observed in teeth. Brackets are typically manufactured in specific dimensions, with the most common sizes of brackets having working surfaces (slots) in 0.018 inch and 0.022 inch dimensions. Either of these measurements allows for an arch wire of similar dimension to be placed in the slot and used to assist in the movement of teeth. In addition, orientation dots may be placed by the bracket manufacturer at the distogingival wing of each bracket to reduce vertical orientation problems during the bonding process.

Orthodontic brackets are typically attached to teeth (bonded) with composite resin at the facial or lingual (palatal) side of the teeth to be moved, and the operator uses the orientation dot to assist in proper bracket orientation. The orthodontic arch wire passes through the arch wire slot and is positioned within the mid-portion of the bracket. This bracket/arch-wire interface allows for movement of teeth within the confines and shape of the wire and the overall prescription of each bracket. Proper orthodontic bracket placement is second only to appropriate orthodontic diagnosis in the overall scheme of standardized orthodontic treatment. There is significant scientific and clinical evidence to indicate that appropriate and well-planned orthodontic tooth movement is less likely to occur if bracket placement is not precise and carefully controlled. Furthermore, the primary problem in correctly bonding brackets directly to teeth is " . . . that the dentist must be able to judge the proper position for the attachment and must carry it to place rapidly and accurately". *Contemporary Orthodontics*, Proffit, W. R. (editor), $2^{nd}$ edition, (1993), the entire contents and disclosure of which is hereby incorporated by reference herein. For example, improper bracket placement may result in (1) improper tooth movement, (2) worsening of occlusal and periodontal conditions, and (3) potential problems in the development of dental caries at bracket sites.

Therefore, there is still a need for an orthodontic bracket placement device and method of bracket placement that may improve bracket placement and subsequently improve the overall accuracy of orthodontic tooth movement.

SUMMARY OF THE INVENTION

It is therefore an object of the present invention to provide a bracket placement device that allows for specific positioning of each bracket based upon measurements found to be beneficial for tooth movement and orthodontic positioning of the teeth.

It is a further object of the present invention to provide a coordinated bracket placement method to provide for proper bracket placement and positioning.

It is a further object of the present invention to provide saleable kits including a bracket placement device.

According to a first broad aspect of the present invention, there is provided an orthodontic bracket placement device comprising a horizontal bracket engaging means for engaging an orthodontic bracket; and a vertical shaft extending from the horizontal bracket engaging means, the shaft including a plurality of indicia for aligning with the incisal edge of a tooth when the bracket placement device is used to place an orthodontic bracket engaged by the engaging means on the tooth.

According to second broad aspect of the invention, there is provided a method for placing an orthodontic bracket on a tooth comprising placing the orthodontic bracket on the tooth at a particular vertical position on the tooth using a bracket placement device by engaging a horizontal bracket engaging means of the device with a bracket and aligning one of a plurality of indicia on the bracket placement device with the incisal edge of the tooth; and adhering the orthodontic bracket to the tooth.

According to a third broad aspect of the invention, there is provided a saleable kit comprising at least one orthodontic bracket placement device comprising a horizontal bracket engaging means for engaging an orthodontic bracket; and a vertical shaft extending from the horizontal bracket engaging means, the shaft including a plurality of indicia for aligning with the incisal edge of a tooth when the bracket placement device is used to place an orthodontic bracket engaged by the engaging means on the tooth.

Other objects and features of the present invention will be apparent from the following detailed description.

BRIEF DESCRIPTION OF THE DRAWINGS

The invention will be described in conjunction with the accompanying drawings, in which.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "prescription" refers to the angulation and orientation of an orthodontic bracket.

For the purposes of the present invention, the term "distogingival" refers to the lower, left-most region or direction of a bracket.

For the purposes of the present invention, the term "incisal edge" refers to the cutting edge of a tooth.

For the purposes of the present invention, the term "bracket" refers to any standard or non-standard/custom orthodontic or dental bracket.

For the purposes of the present invention, when referring to a tooth, the term "long axis" refers to the axis of a tooth measured from the incisal edge to the root along the midline.

For the purposes of the present invention, the term "stop" refers to a device used to prevent an orthodontic or dental instrument from moving passed a certain point or used to indicate when such an instrument has reached a predetermined point.

For the purposes of the present invention, the term "tip" refers to a defined bracket angulation that is other than square.

For the purposes of the present invention, the term "orientation dot" refers to a mark that appears on a bracket to indicate a particular bracket prescription and used to assist in orienting the bracket properly on a tooth.

For the purposes of the present invention, the term "wing" refers to a raised region located in each corner of a bracket.

For the purposes of the present invention, when referring to a tooth, the terms "facial aspect" refers to the front-side of a tooth.

For the purposes of the present invention, the term "sidedness" refers to the appropriate bracket (left incisor, for example) being placed on the correct tooth due to the prescription requirements of that particular tooth and the corresponding bracket for that tooth.

Description

Figure 1:
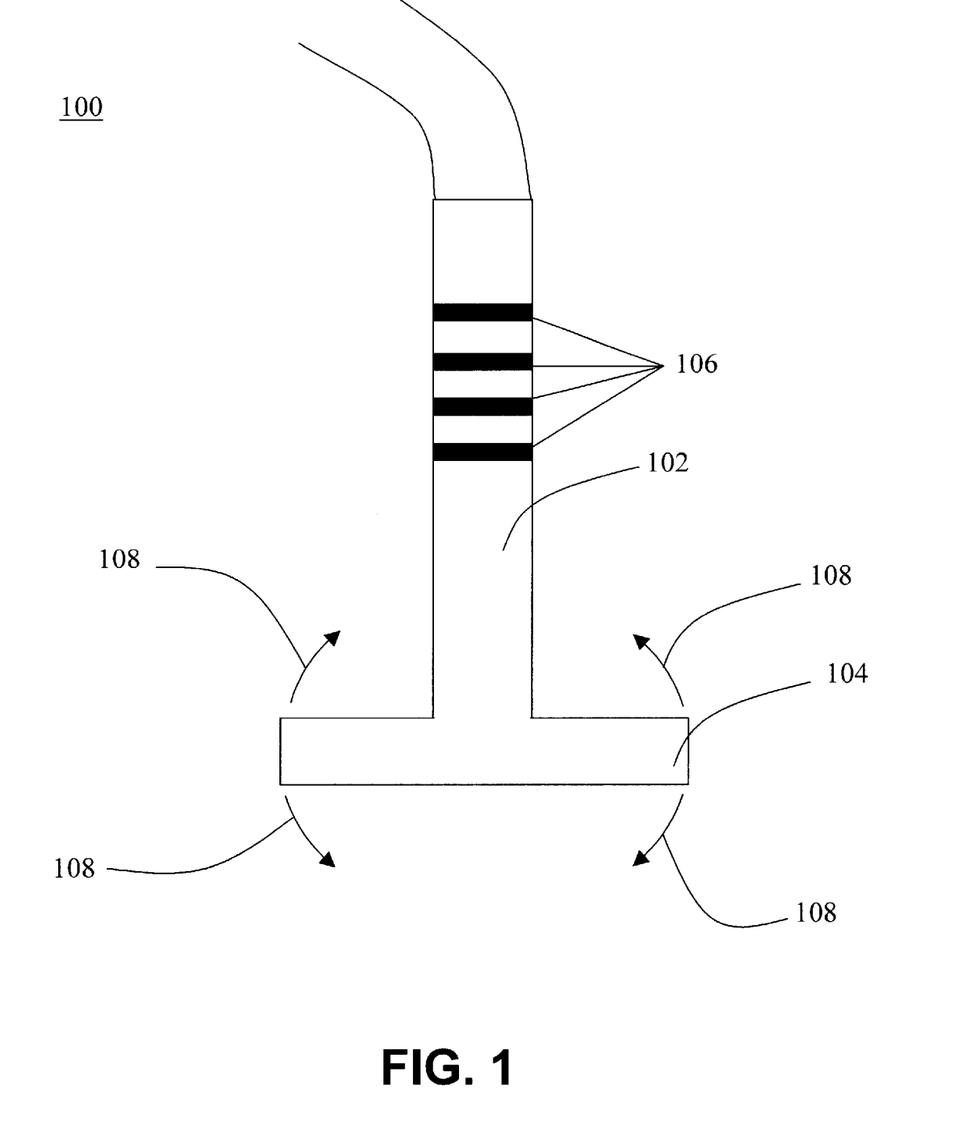
FIG. 1 is a schematic illustration of a bracket placement device constructed in accordance with an embodiment of the present invention.

FIG. 1 illustrates an orthodontic bracket placement device 100 according to the present invention. Device 100 has a vertical shaft 102 and a horizontal bracket engaging means 104. The identifiers "vertical" and "horizontal" are for illustrative purposes only and refer to the typical orientation of device 100 when in use. Vertical placement bands 106 represent vertical placement prescriptions for brackets. Each band 106 represents a different desired placement height of a bracket on a tooth.

Vertical placement bands of the present invention may be etched into the shaft of the bracket placement device and/or may include visible indicia, markers, numbers, colors, etc. In a preferred embodiment of the present invention, the bands are each of a different color and may correspond to colors on particular brackets. The bands may be made to glow in the dark or to react to UV or other light stimulation. Although four bands are illustrated in FIG. 1, it should be understood that any number of bands may be placed on a shaft of a device according to the present invention. The bands may correspond to standard bracket prescriptions or may correspond to non-standard/custom heights.

The angle formed between vertical shaft 102 and horizontal bracket engaging means 104 is represented in FIG. 1 as 90°. However, as is indicated by arrows 108, horizontal bracket engaging means 104 may be formed on vertical shaft 102 such that the angle is from about 70° to about 110°, such as 70°, 75°, 80°, 85°, 95°, 100°, 105°, 110° or any other suitable angle, to allow for versatility and use with brackets having prescriptions requiring the angle to be other than 90°. This variation allows a device of the present invention to be constructed based on various manufacturers' prescriptions and thus accounts for a desired bracket tip.

The placement end or proximal end of an orthodontic bracket placement device of the present invention is defined by the junction of a vertical shaft and a horizontal bracket engaging means. At the opposite end or distal end of an orthodontic bracket placement device of the present invention, any suitable orthodontic or dental tool may be included, such as a dental scaler, mirror, etc.

Figure 2:
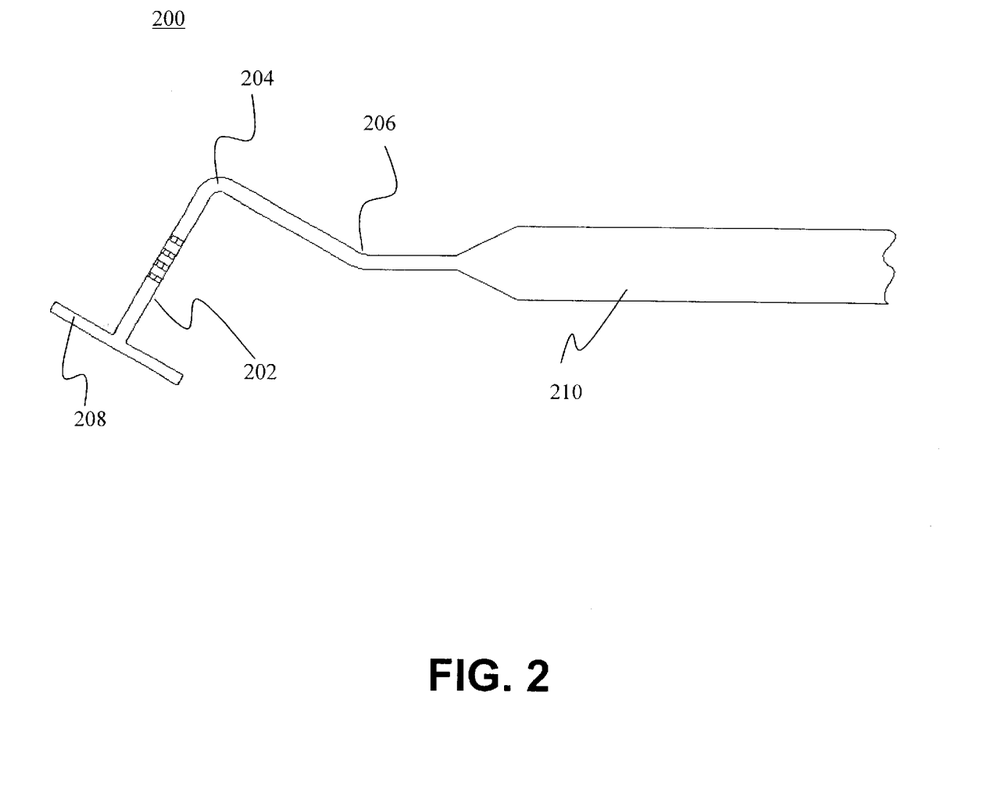
FIG. 2 illustrates a bracket placement device constructed in accordance with an embodiment of the present invention.

FIG. 2 illustrates an embodiment of an orthodontic bracket placement device 200 of the present invention. As may be seen in FIG. 2, vertical shaft portion 202 of device 200 is formed with bends 204 and 206 between horizontal bracket engaging means 208 and handle 210. Bends 204 and 206 are formed to provide a level of comfort with respect to a user's angle of approach to a patient's mouth. It should be understood that bends 204 and 206 are illustrative and may be modified in number and degree to allow for various angles and orientations of device 200.

Orthodontic bracket placement devices of the present invention may be constructed of any suitable material for dental and/or orthodontic devices, including, but not limited to metal, such as stainless steel, and polymeric materials, such as plastics. Metals, such as stainless steel, are beneficial in that devices constructed from such materials may be sterilized and reused. Polymeric materials, such as plastics, are beneficial in that devices constructed from such materials may be made transparent to allow for better visualization of the teeth on which the dentist/orthodontist is working. In addition, plastic devices may be single-use. In particular embodiments of the present invention, the device is preferably rigid in construction.

Devices of the present invention may be made from a single piece of material (i.e., unibody), or may be multiple pieces that are put together, either before or after manufacture, by welding, screws, etc. For example, a horizontal bracket engaging means may screw into one end of a vertical shaft. Thus, a single vertical shaft could be used for multiple horizontal bracket engaging means, for example, each having a different tip or prescription.

Figure 3:
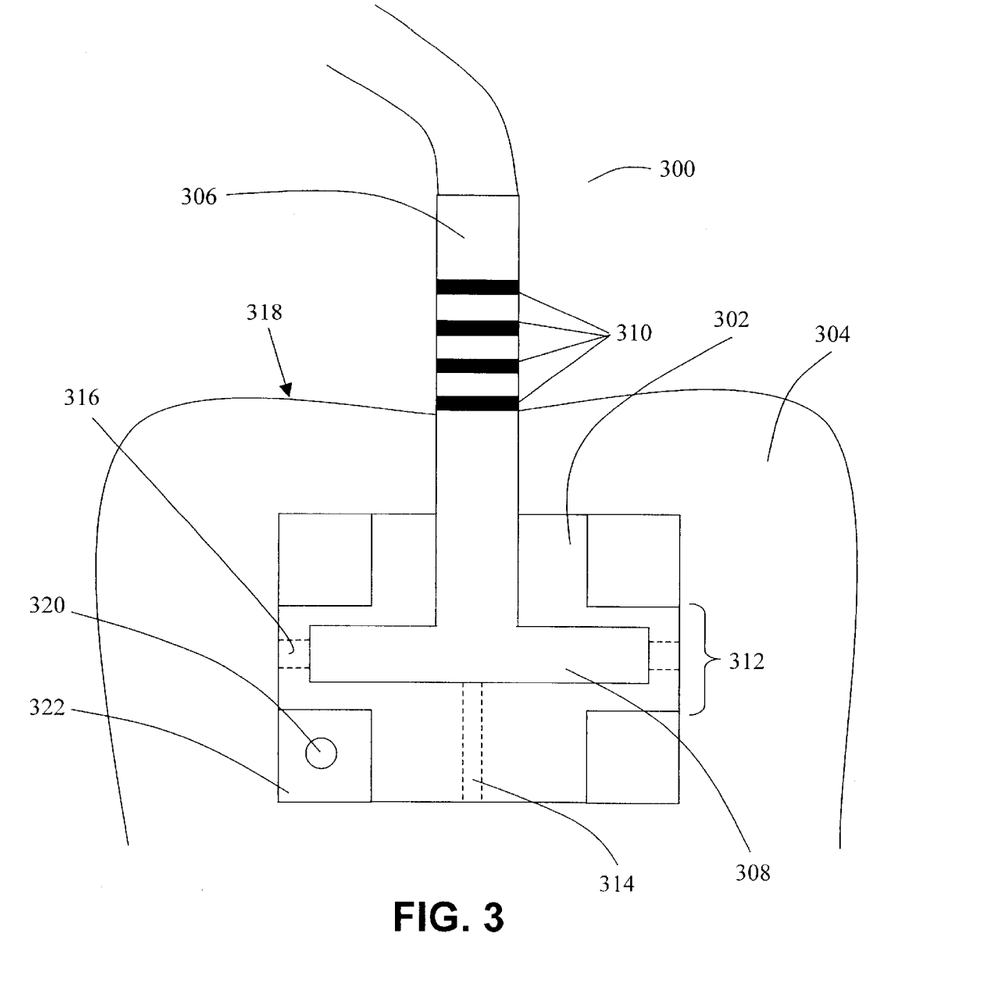
FIG. 3 is a schematic illustration of a bracket placement method of the present invention with a bracket placement device of the present invention engaged with a coordinated bracket.

FIG. 3 illustrates an orthodontic bracket placement device 300 according to the present invention being used to place a coordinated bracket 302 on a tooth 304. Device 300 has a vertical shaft 306 and a horizontal bracket engaging means 308. The identifiers "vertical" and "horizontal" are for illustrative purposes only and refer to the typical orientation of device 300 when in use. Vertical placement bands 310 represent vertical placement prescriptions for brackets. Each band 310 represents a different placement height of a bracket on a tooth.

Bracket 302 has a horizontal arch wire slot 312. Horizontal bracket engaging means 308 fits within arch wire slot 312 to allow the user to apply pressure to bracket 302 against tooth 304 and to move bracket 302 into the proper location. A horizontal bracket engaging means of the present invention may be made to fit into any standard arch wire slot, such as 0.022 inches or 0.018 inches, or to fit into any custom arch wire slot. A horizontal bracket engaging means of the present invention may be longer than, shorter than, or the same length as the width of the bracket.

Bracket 302 may also have vertical alignment markings 314 and/or horizontal alignment markings 316. Markings 314 and 316 may be etched into bracket 302 or may be lines or colors to provide a reference line for proper alignment.

In use, horizontal bracket engaging means 308 is inserted into arch wire slot 312. Bracket 302 is placed against tooth 304, preferably on the facial aspect of tooth 304, and moved into a proper position. A suitable dental or orthodontic adhesive is used to hold bracket 302 in place. To determine proper horizontal placement of bracket 302, the user identifies the long axis of the tooth and aligns bracket 302 and vertical shaft 306 along the long axis of the tooth. Optional vertical alignment markings may assist in aligning vertical shaft 306 properly. For proper vertical placement, the user identifies the desired vertical placement for the particular tooth and bracket and aligns the band 310 that corresponds to the desired vertical placement with the incisal edge 318 of tooth 304. To ensure the proper placement, bracket 302 may have an orientation dot 320 located on a wing 322 of bracket 302 that is colored, etched, or otherwise distinguishable from other such markings. In embodiments of the present invention, orientation dot 320 corresponds to indicia, markings, colors etc. on bands 310. Thus, to achieve the desired vertical placement of bracket 302, the user aligns band 310 having the same color or other marking as orientation dot 320 with incisal edge 318 of tooth 304.

Figure 4:
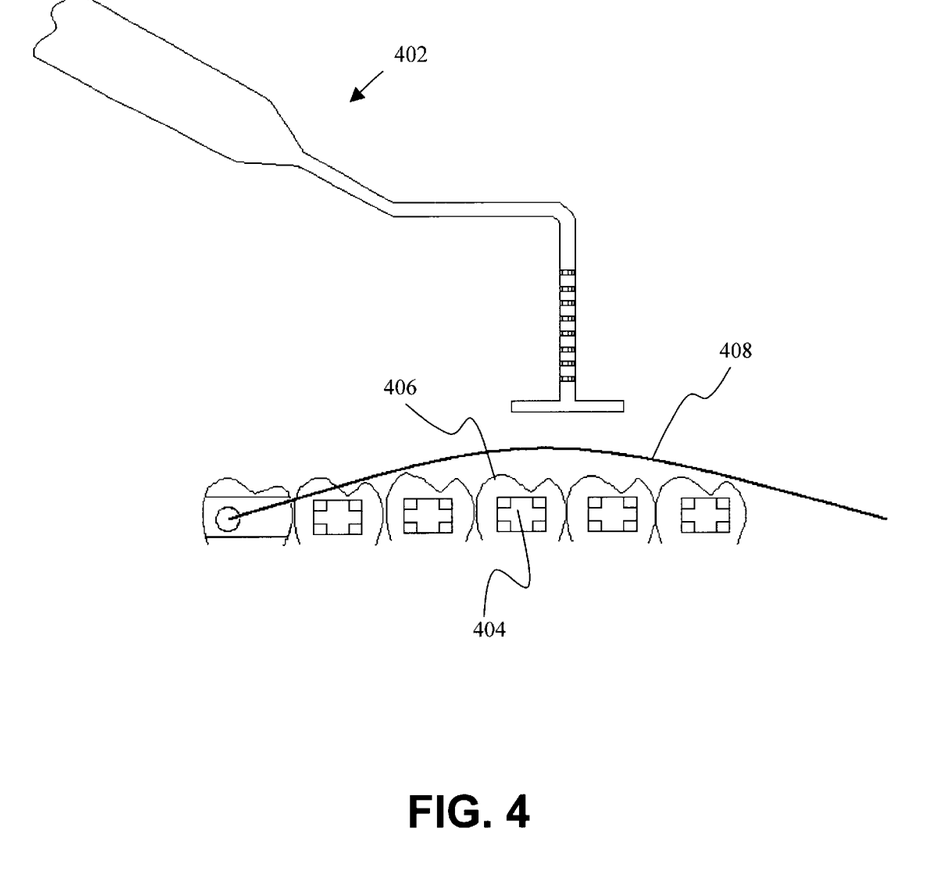
FIG. 4 illustrates a bracket placement method of the present invention with a bracket placement device of the present invention in use.
Figure 5:
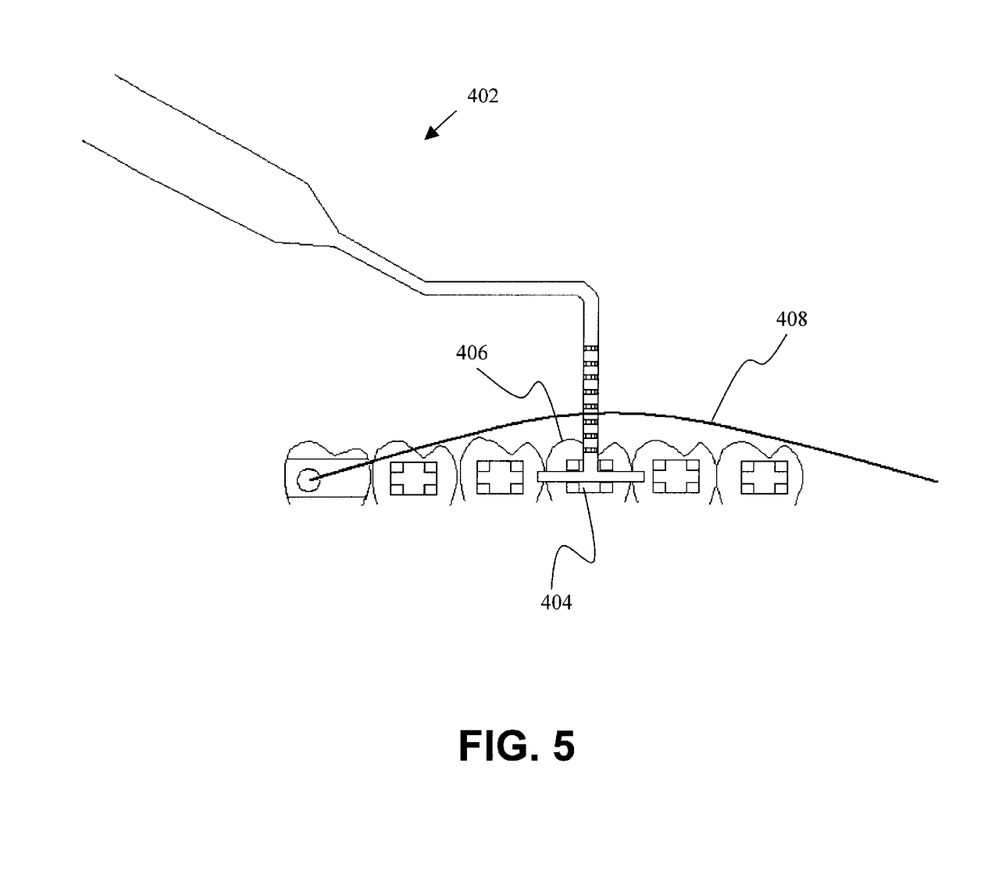
FIG. 5 illustrates a bracket placement method of the present invention with a bracket placement device of the present invention engaged with a bracket.

FIGS. 4 and 5 illustrate the use of an embodiment of an orthodontic bracket placement device of the present invention. As outlined above, a bracket placement device 402 of the present invention may be used to engage an orthodontic bracket 404 and allow a user to move bracket 404 into a proper location. A bracket placement device 402 of the present invention allows for proper vertical and horizontal placement, as well as proper orientation and angulation of a bracket 404 on a tooth 406. Bracket placement device 402 may be used to align a bracket 404 to allow for proper insertion of arch wire 408 into a bracket 404.

Figure 6:
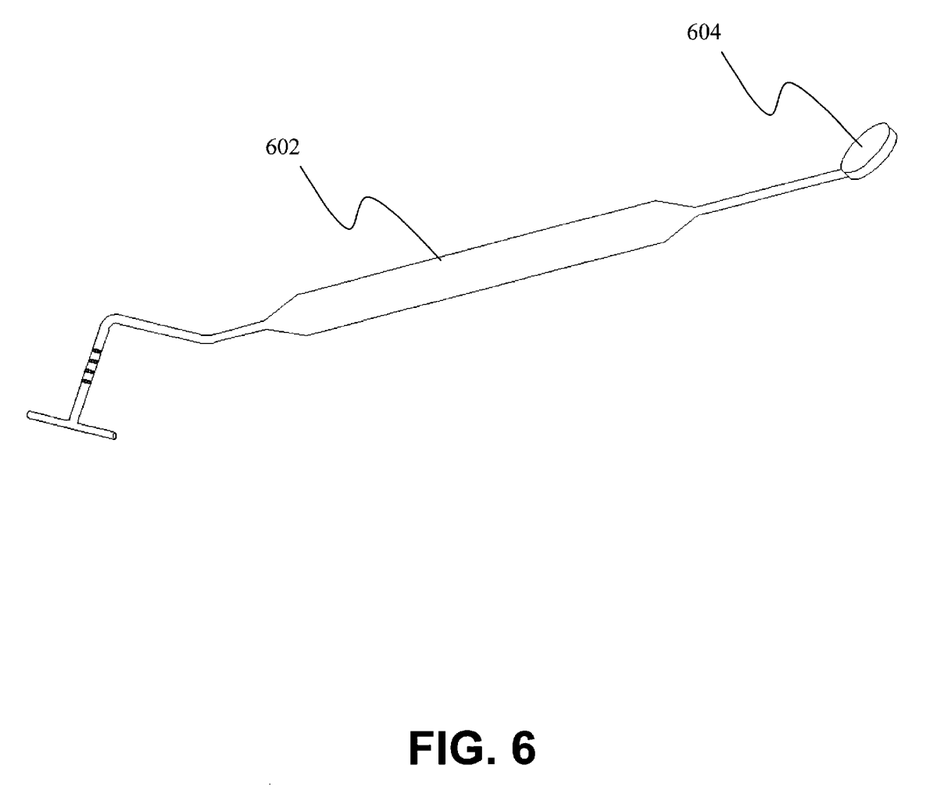
FIG. 6 illustrates a bracket placement device of the present invention with a mirror on one end.
Figure 7:
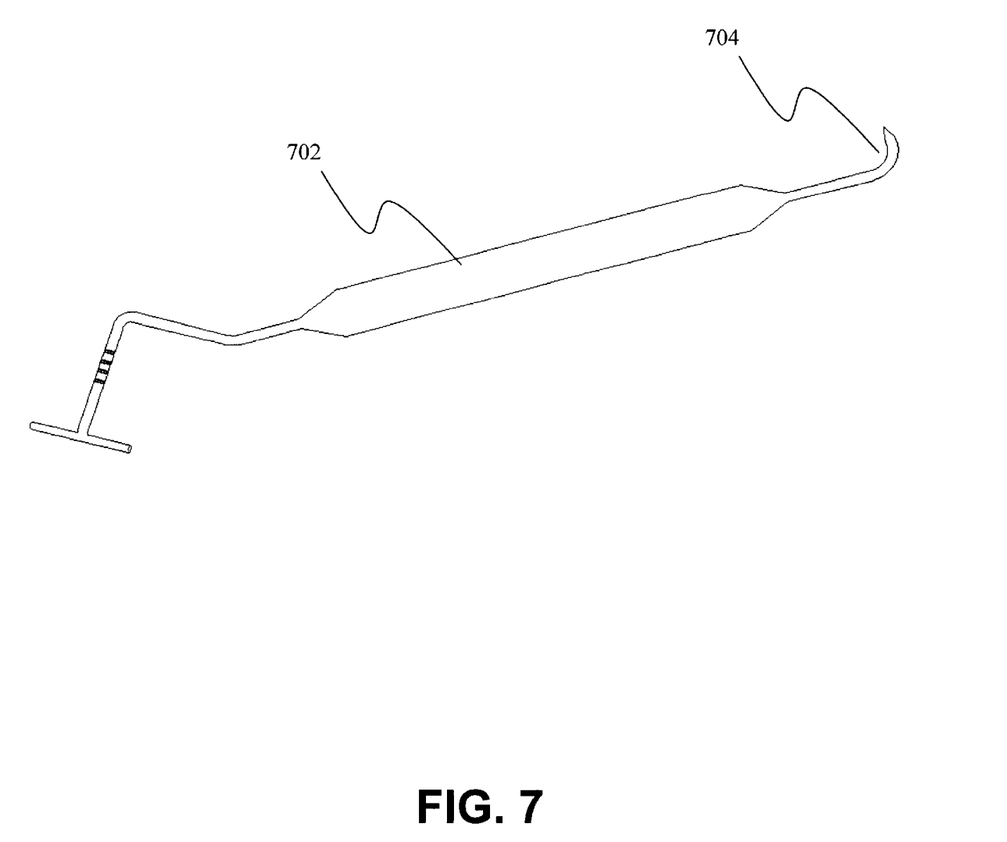
FIG. 7 illustrates a bracket placement device of the present invention with a dental scaler on one end.

FIGS. 6 and 7 show alternate embodiments of a bracket placement device of the present invention. FIG. 6 shows a bracket placement device 602 having a mirror 604 on one end of bracket placement device 602. FIG. 7 shows a bracket placement device 702 having a dental scaler 704 on one end of bracket placement device 702.

Figure 8:
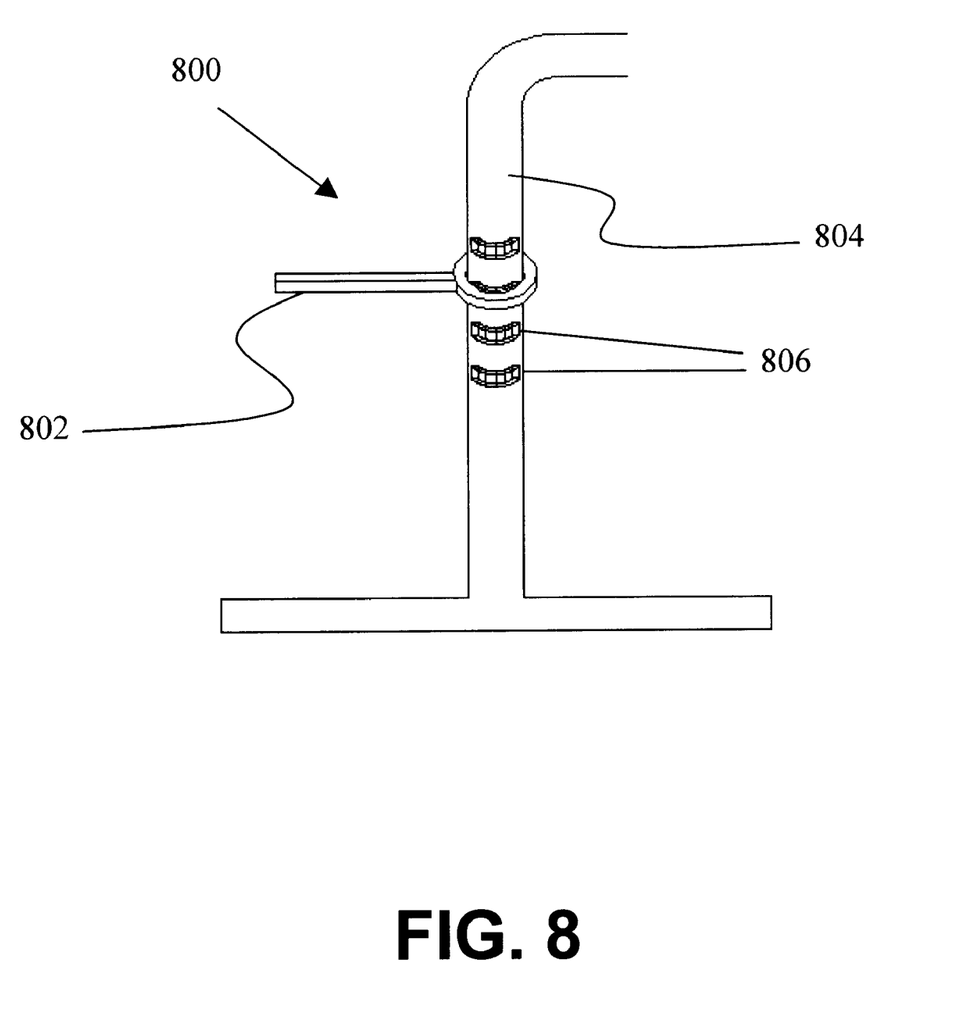
FIG. 8 illustrates a dental stop according to an embodiment of the present invention.

According to an embodiment of the present invention as shown in FIG. 8, an orthodontic bracket placement device of the present invention may include a stop or stops 800 to assist the user in making accurate placement determinations. An example of a suitable stop 800 is a slidable device having an extension 802 that extends over the incisal edge of a tooth. Such a slidable device may be moved up and down a shaft 804 of a bracket placement device of the present invention and may engage with bands 806 on the placement device. When engaged with a band 806 corresponding to the desired height, the user would align extension 802 of stop 800 with the incisal edge of the tooth. Such a stop would assist the user in making the proper height determination. Any other suitable dental or orthodontic stop may be used with the present invention.

Figure 9:
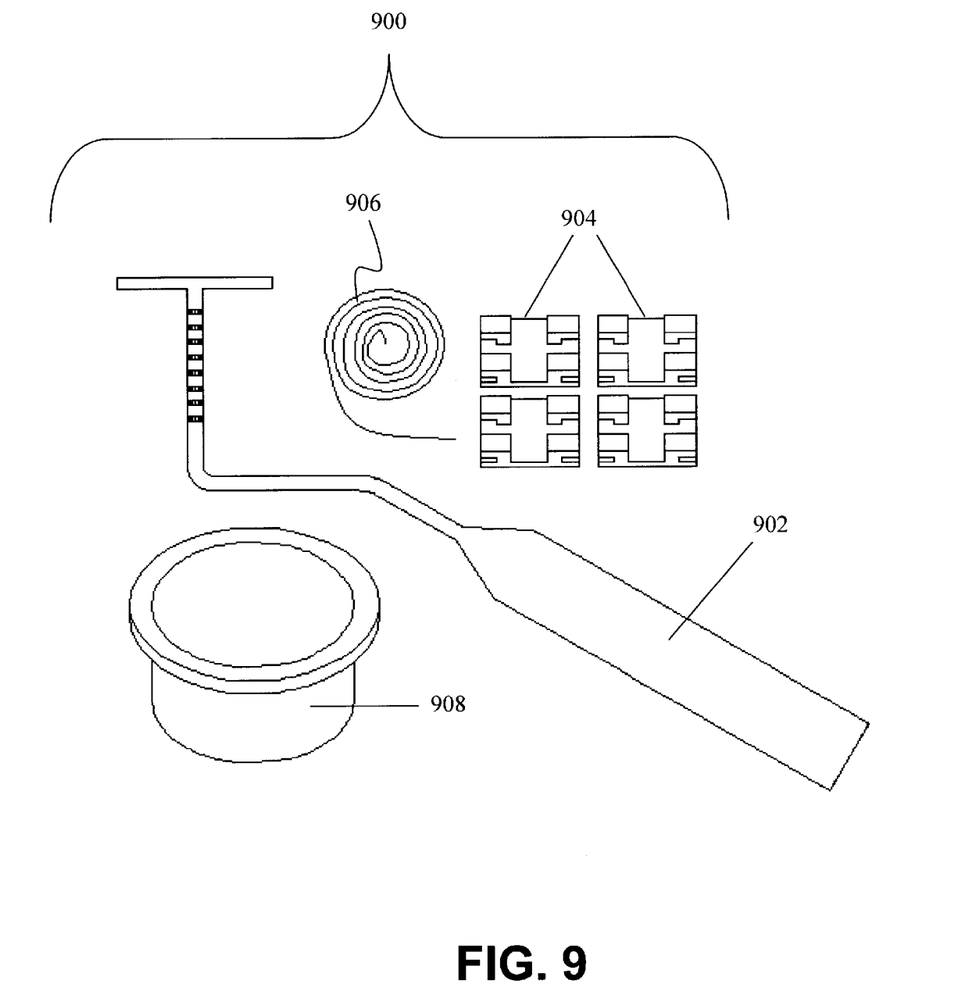
FIG. 9 illustrates a kit according to an embodiment of the present invention.

The present invention also provides for saleable kits. As shown in FIG. 9. a kit 900 of the present invention may include a bracket placement device of the present invention 902, at least one bracket 904, arch wire 906, and/or adhesive 908. In an embodiment of the present invention, the components of the kit may be individually sterilized and/or the entire kit may be sterilized.

EXAMPLES

Example I

A bracket placement device of the present invention was constructed with a 0.016 inch×0.022 inch stainless steel horizontal bracket engaging means. The stainless steel bracket engaging means was constructed to be approximately the width of a standard orthodontic bracket, and narrow enough gingivally and incisally so as to fit within the arch wire slot of a standard 0.022 inch and 0.018 inch orthodontic bracket. The shaft of the device is marked in colors (see below) at specific distances from the junction of the vertical shaft and the horizontal 0.016 inch×0.022 inch stainless steel bracket engaging means. The measurements on the shaft are 3.5 mm, 4.0 mm, 4.5 mm, and 5.0 mm. Standardized measurements for proper placement of brackets have been established at the following distances from the middle of an arch wire slot to the incisal edge of an associated tooth:

| Tooth Number | 6 | 5 | 4 | 3 | 2 | 1 | 1 | 2 | 3 | 4 | 5 | 6 |
| --- | --- | --- | --- | --- | --- | --- | --- | --- | --- | --- | --- | --- |
| Maxillary Arch: | | | | | | | | | | | | |
| Position (in mm from incisal edge) | 4 | 4 | 4 | 5 | 4 | 4.5 | 4.5 | 4 | 5 | 4 | 4 | 4 |
| Mandibular Arch: | | | | | | | | | | | | |
| Position (in mm from incisal edge) | 4 | 4 | 4 | 4.5 | 4 | 4 | 4 | 4 | 4.5 | 4 | 4 | 4 |

These specific measurements help insure the appropriate vertical, horizontal, and lingual orientation and final positioning of teeth following orthodontic treatment. If these dimensions are not used, the manufactured prescription for the brackets will not be "filled" or carried out, and a random alignment of the teeth can be anticipated as a direct result of inappropriate and substandard treatment.

As mentioned above, the colored markings on the shaft correspond with the same color orientation dot on the distogingival wing of each bracket. In other words, since each bracket has been assigned a specific position vertically from the incisal edge of the tooth to the mid portion of the bracket slot by the bracket manufacturer in order to best "fill" the individual bracket-tooth prescription, the selected color on the measuring shaft corresponds to that particular bracket and its vertical specifications for that tooth. For this example, randomly chosen colors have been assigned to specific measurements required for proper bracket placement:

3.5 mm=red
4.0 mm=blue
4.5 mm=black
5.0 mm=green

If a bracket has been manufactured for placement on a tooth having a 4.0 mm incisal-edge/bracket-slot dimension, that specific bracket will have a "blue" orientation dot. That is, each color on the shaft of the bracket placement device will correspond to the prescribed vertical prescription for each bracket having the same colored orientation dot as the appropriate increment on the bracket placement device. The vertical shaft of the bracket placement device is used to align the bracket along the long axis of each tooth and the horizontal bracket engaging means of the device fits within the arch wire slot of each bracket to allow for precise vertical height adjustment as well as orientation along the long axis of the tooth being bracketed.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An orthodontic bracket placement device comprising:
   a horizontal bracket engaging means for engaging an orthodontic bracket; and
   a vertical shaft extending from said horizontal bracket engaging means, said shaft including a plurality of indicia for aligning with the incisal edge of a tooth when said bracket placement device is used to place an orthodontic bracket engaged by said engaging means on said tooth, wherein said horizontal bracket engaging means and said vertical shaft form a substantially T-shaped junction.

2. The device of claim 1, wherein said plurality of indicia comprises lines.

3. The device of claim 2, wherein said lines have at least two different colors.

4. The device of claim 3, wherein said at least two different colors each indicate a different specific vertical placement of said orthodontic bracket on said tooth.

5. The device of claim 1, wherein said plurality of indicia are etched into said shaft.

6. The device of claim 1, wherein said plurality of indicia glow in the dark.

7. The device of claim 1, wherein said horizontal bracket engaging means is at an angle of between about 70° and; about 110° with respect to said vertical shaft.

8. The device of claim 1, wherein said horizontal bracket engaging means is at an angle of substantially 90° with respect to said vertical shaft.

9. The device of claim 1, wherein said device comprises stainless steel.

10. The device of claim 1, wherein said device comprises a polymeric material.

11. The device of claim 1, wherein said device is of unibody construction.

12. The device of claim 1, wherein said plurality of indicia each indicate a different specific vertical placement of said orthodontic bracket on said tooth.

13. The device of claim 12, wherein said plurality of indicia correspond to bracket placements of 3.5 mm, 4.0 mm, 4.5 mm and 5.0 mm measured from the incisal edge of said tooth.

14. The device of claim 1, further comprising a stop disposed on said vertical shaft.

15. A method for placing an orthodontic bracket on a tooth comprising:

placing said orthodontic bracket on said tooth at a particular vertical position on said tooth using a bracket placement device by engaging a horizontal bracket engaging means of said device with a bracket and aligning one of a plurality of indicia on a vertical shaft of said bracket placement device with the incisal edge of said tooth. wherein said horizontal bracket engaging means and said vertical shaft form a substantially T-shaped junction; and adhering said orthodontic bracket to said tooth.

16. The method of claim 15, wherein said plurality of indicia comprises lines.

17. The method of claim 16, wherein said lines have at least two different colors.

18. The method of claim 17, wherein said at least two different colors each indicate a different specific vertical placement of said orthodontic bracket on said tooth.

19. The method of claim 18, wherein one of said at least two different colors corresponds to a color located on said bracket.

20. The method of claim 19, wherein said color located on said bracket is located on a wing of said bracket.

21. The method of claim 20, wherein said wing is the distogingival wing of said bracket.

22. The method of claim 15, wherein said plurality of indicia are etched into a vertical shaft of said device.

23. The method of claim 15, wherein said plurality of indicia glow in the dark.

24. The method of claim 15, wherein said horizontal bracket engaging means is at an angle of between about 70° and about 110° with respect to a vertical shaft of said device.

25. The method of claim 15, wherein said horizontal bracket engaging means is at an angle of substantially 90° with respect to a vertical shaft of said device.

26. The method of claim 15, wherein said plurality of indicia each indicate a different specific vertical placement of said orthodontic bracket on said tooth.

27. The method of claim 26, wherein said plurality of indicia correspond to bracket placements of 3.5 mm, 4.0 mm, 4.5 mm and 5.0 mm measured from the incisal edge of said tooth.

28. The method of claim 15, further comprising a stop disposed on a vertical shaft of said device.

29. The method of claim 28, wherein said stop is engaged with a region of said device having said plurality of indicia and said stop is aligned with the incisal edge of said tooth.

30. A saleable kit comprising:
   at least one orthodontic bracket placement device comprising a horizontal bracket engaging means for engaging an orthodontic bracket; and a vertical shaft extending from said horizontal bracket engaging means, said shaft including a plurality of indicia for aligning with the incisal edge of a tooth when said bracket placement device is used to place an orthodontic bracket engaged by said engaging means on said tooth, wherein said horizontal bracket engaging means and said vertical shaft form a substantially T-shaped junction.

31. The kit of claim 30, wherein said kit is sterilized.

32. The kit of claim 30, further comprising at least one bracket.

33. The kit of claim 32, wherein said kit is sterilized.

34. The kit of claim 30, further comprising arch wire.

35. The kit of claim 34, wherein said kit is sterilized.

36. The kit of claim 30, further comprising dental adhesive.

37. The kit of claim 34, wherein said kit is sterilized.

38. The kit of claim 30, wherein said plurality of indicia comprises lines.

39. The kit of claim 38, wherein said lines have at least two different colors.

40. The kit of claim 39, wherein said at least two different colors each indicate a different specific vertical placement of said orthodontic bracket on said tooth.

41. The kit of claim 40, further comprising at least one bracket.

42. The kit of claim 41, wherein one of said at least two different colors corresponds to a color located on said bracket.

43. The kit of claim 42, wherein said color located on said bracket is located on a wing of said bracket.

44. The kit of claim 43, wherein said wing is the distogingival wing of said bracket.

45. The kit of claim 30, wherein said plurality of indicia are etched into said shaft.

46. The kit of claim 30, wherein said plurality of indicia glow in the dark.

47. The kit of claim 30, wherein said horizontal bracket engaging means is at an angle of between about 70° and about 110° with respect to said vertical shaft.

48. The kit of claim 30, wherein said horizontal bracket engaging means is at an angle of substantially 90° with respect to said vertical shaft.

49. The kit of claim 30, wherein said device comprises stainless steel.

50. The kit of claim 30, wherein said device comprises a polymeric material.

51. The kit of claim 30, wherein said device is of unibody construction.

52. The kit of claim 30, wherein said plurality of indicia each indicate a different specific vertical placement of said orthodontic bracket on said tooth.

53. The kit of claim 52, wherein said plurality of indicia correspond to bracket placements of 3.5 mm, 4.0 mm, 4.5 mm and 5.0 mm measured from the incisal edge of said tooth.

54. The kit of claim 30, further comprising a stop disposed on said vertical shaft.

55. An orthodontic bracket placement device comprising:

a horizontal bracket engaging means for engaging an orthodontic bracket;

a vertical shaft extending from said horizontal bracket engaging means, said shaft including a plurality of indicia for aligning with the incisal edge of a tooth when said bracket placement device is used to place an orthodontic bracket engaged by said engaging means on said tooth; and a dental scaler located at an end of the device opposite to a junction formed between said horizontal bracket engaging means and said vertical shaft.

56. An orthodontic bracket placement device comprising:

a horizontal bracket engaging means for engaging an orthodontic bracket;

a vertical shaft extending from said horizontal bracket engaging means, said shaft including a plurality of indicia for aligning with the incisal edge of a tooth when said bracket placement device is used to place an orthodontic bracket engaged by said engaging means on said tooth; and a mirror located at an end of the device opposite to a junction formed between said horizontal bracket engaging means and said vertical shaft.

57. A saleable kit comprising:

at least one orthodontic bracket placement device comprising a horizontal bracket engaging means for engaging an orthodontic bracket; a vertical shaft extending from said horizontal bracket engaging means, said shaft including a plurality of indicia for aligning with the incisal edge of a tooth when said bracket placement device is used to place an orthodontic bracket engaged by said engaging means on said tooth; and a dental scaler located at an end of the device opposite to a junction formed between said horizontal bracket engaging means and said vertical shaft.

58. A saleable kit comprising:

at least one orthodontic bracket placement device comprising a horizontal bracket engaging means for engaging an orthodontic bracket; a vertical shaft extending from said horizontal bracket engaging means, said shaft including a plurality of indicia for aligning with the incisal edge of a tooth when said bracket placement device is used to place an orthodontic bracket engaged by said engaging means on said tooth; and a mirror located at an end of the device opposite to a junction formed between said horizontal bracket engaging means and said vertical shaft.

* * * * *